United States Patent
Clubb et al.

(10) Patent No.: US 8,137,376 B2
(45) Date of Patent: ***Mar. 20, 2012

(54) EMBOLIC FILTERS HAVING MULTIPLE LAYERS AND CONTROLLED PORE SIZE

(75) Inventors: Thomas L. Clubb, Hudson, WI (US);
John C. Oslund, Blaine, MN (US);
Richard S. Kusleika, Eden Prairie, MN (US)

(73) Assignee: Tyco Healthcare Group LP, Mansfield, MA (US)

( * ) Notice: Subject to any disclaimer, the term of this patent is extended or adjusted under 35 U.S.C. 154(b) by 1108 days.

This patent is subject to a terminal disclaimer.

(21) Appl. No.: 11/789,851

(22) Filed: Apr. 26, 2007

(65) Prior Publication Data

US 2007/0198051 A1   Aug. 23, 2007

Related U.S. Application Data

(63) Continuation of application No. 10/354,829, filed on Jan. 30, 2003, now Pat. No. 7,220,271.

(51) Int. Cl.
*A61M 29/00* (2006.01)
(52) U.S. Cl. ..................... 606/200; 604/96.01
(58) Field of Classification Search .................. 606/127, 606/159, 200; 604/96, 280, 96.01, 101, 264
See application file for complete search history.

(56) References Cited

U.S. PATENT DOCUMENTS

| | | | |
|---|---|---|---|
| 3,690,606 A | 9/1972 | Pall | |
| 4,425,908 A | 1/1984 | Simon | |
| 4,619,246 A | 10/1986 | Molgaard-Nielsen et al. | |
| 4,640,778 A * | 2/1987 | Blomback et al. ............ | 210/484 |
| 4,789,410 A | 12/1988 | Parizek | |
| 4,864,329 A | 9/1989 | Kneezel et al. | |
| 5,188,734 A | 2/1993 | Zepf | |
| 5,814,064 A | 9/1998 | Daniel et al. | |
| 5,855,598 A | 1/1999 | Pinchuk | |
| 5,901,775 A | 5/1999 | Musschoot et al. | |
| 5,919,224 A | 7/1999 | Thompson et al. | |
| 6,001,118 A | 12/1999 | Daniel et al. | |
| 6,019,784 A | 2/2000 | Hines | |
| 6,053,932 A | 4/2000 | Daniel et al. | |
| 6,059,814 A | 5/2000 | Ladd | |
| 6,066,149 A | 5/2000 | Samson et al. | |

(Continued)

FOREIGN PATENT DOCUMENTS

EP   0 350 043 A1   1/1990

(Continued)

OTHER PUBLICATIONS

Search Report for International Application No. PCT/US2004/002587.

(Continued)

*Primary Examiner* — Victor Nguyen

(57) ABSTRACT

The invention provides a device for filtering emboli from blood flowing through a lumen defined by the walls of a vessel in a patient's body including a filter element. The filter element is expandable from a collapsed configuration to an expanded configuration. When the filter element is in the expanded configuration, the average pore size is from 30 to 300 microns and the standard deviation of the pore size is less than 20 percent of the average pore size. The filter element has two or more filtering layers, each filtering layer having pores, and each filtering layer being adjacent to at least one other filtering layer.

34 Claims, 18 Drawing Sheets

U.S. PATENT DOCUMENTS

| | | | |
|---|---|---|---|
| 6,123,715 A | 9/2000 | Amplatz | |
| 6,129,739 A | 10/2000 | Khosravi | |
| 6,179,859 B1 | 1/2001 | Bates et al. | |
| 6,179,861 B1 | 1/2001 | Khosravi et al. | |
| 6,203,732 B1 | 3/2001 | Clubb et al. | |
| 6,206,868 B1 | 3/2001 | Parodi | |
| 6,210,500 B1 | 4/2001 | Zurfluh | |
| 6,214,026 B1 | 4/2001 | Lepak et al. | |
| 6,245,089 B1 | 6/2001 | Daniel et al. | |
| 6,277,139 B1 | 8/2001 | Levinson et al. | |
| 6,312,407 B1 | 11/2001 | Zadno-Azizi et al. | |
| 6,325,815 B1 * | 12/2001 | Kusleika et al. | 606/200 |
| 6,336,934 B1 | 1/2002 | Gilson et al. | |
| 6,346,116 B1 | 2/2002 | Brooks et al. | |
| 6,361,545 B1 | 3/2002 | Macoviak et al. | |
| 6,364,895 B1 | 4/2002 | Greenhalgh | |
| 6,368,339 B1 | 4/2002 | Amplatz | |
| 6,383,171 B1 | 5/2002 | Gifford et al. | |
| 6,383,196 B1 | 5/2002 | Leslie et al. | |
| 6,391,044 B1 | 5/2002 | Yadav et al. | |
| 6,409,750 B1 | 6/2002 | Hyodoh et al. | |
| 6,425,909 B1 | 7/2002 | Dieck et al. | |
| 6,461,370 B1 | 10/2002 | Gray et al. | |
| 6,485,501 B1 | 11/2002 | Green | |
| 6,494,907 B1 | 12/2002 | Bulver | |
| 6,558,405 B1 | 5/2003 | McInnes | |
| 6,602,271 B2 | 8/2003 | Adams et al. | |
| 6,632,241 B1 | 10/2003 | Hancock et al. | |
| 6,656,203 B2 | 12/2003 | Roth et al. | |
| 6,740,061 B1 | 5/2004 | Oslund et al. | |
| 6,773,448 B2 | 8/2004 | Kusleika et al. | |
| 6,786,919 B1 | 9/2004 | Escano et al. | |
| 6,792,979 B2 | 9/2004 | Konya et al. | |
| 6,969,396 B2 | 11/2005 | Krolik et al. | |
| 7,001,425 B2 | 2/2006 | McCullagh et al. | |
| 7,192,434 B2 | 3/2007 | Anderson et al. | |
| 7,220,271 B2 | 5/2007 | Clubb et al. | |
| 7,323,001 B2 | 1/2008 | Clubb et al. | |
| 2002/0004667 A1 | 1/2002 | Adams et al. | |
| 2002/0022858 A1 | 2/2002 | Demond et al. | |
| 2002/0042627 A1 | 4/2002 | Brady et al. | |
| 2002/0045668 A1 | 4/2002 | Dang et al. | |
| 2002/0045916 A1 | 4/2002 | Gray et al. | |
| 2002/0055747 A1 | 5/2002 | Cano et al. | |
| 2002/0058911 A1 | 5/2002 | Gilson et al. | |
| 2002/0058964 A1 | 5/2002 | Addis | |
| 2002/0091409 A1 | 7/2002 | Sutton et al. | |
| 2002/0107541 A1 | 8/2002 | Vale et al. | |
| 2002/0111648 A1 | 8/2002 | Kusleika et al. | |
| 2002/0115942 A1 | 8/2002 | Stanford et al. | |
| 2002/0128680 A1 | 9/2002 | Pavlovic | |
| 2002/0161392 A1 | 10/2002 | Dubrul | |
| 2002/0161394 A1 | 10/2002 | Macoviak et al. | |
| 2002/0165576 A1 | 11/2002 | Boyle et al. | |
| 2002/0188314 A1 | 12/2002 | Anderson et al. | |
| 2003/0023264 A1 | 1/2003 | Dieck et al. | |
| 2003/0040771 A1 | 2/2003 | Hyodoh et al. | |
| 2003/0176884 A1 | 9/2003 | Berrada et al. | |
| 2003/0187495 A1 * | 10/2003 | Cully et al. | 623/1.15 |
| 2004/0082967 A1 | 4/2004 | Broome et al. | |
| 2004/0153117 A1 | 8/2004 | Clubb et al. | |
| 2004/0153119 A1 | 8/2004 | Kusleika et al. | |
| 2004/0215167 A1 | 10/2004 | Belson | |
| 2005/0192620 A1 | 9/2005 | Cully et al. | |
| 2007/0135834 A1 | 6/2007 | Clubb et al. | |

FOREIGN PATENT DOCUMENTS

| | | |
|---|---|---|
| EP | 0 350 043 B1 | 1/1990 |
| EP | 1 181 900 A2 | 2/2002 |
| EP | 1 226 795 A2 | 7/2002 |
| EP | 1 316 292 A1 | 6/2003 |
| EP | 1 560 544 B1 | 1/2008 |
| WO | WO 94/06372 | 3/1994 |
| WO | WO 96/01591 | 1/1996 |
| WO | WO 97/25002 | 7/1997 |
| WO | WO 98/38920 | 9/1998 |
| WO | WO 98/39053 | 9/1998 |
| WO | WO 99/16382 | 4/1999 |
| WO | WO 00/16705 | 3/2000 |
| WO | WO 00/53119 | 9/2000 |
| WO | WO 00/53120 | 9/2000 |
| WO | WO 00/58964 | 10/2000 |
| WO | WO 00/67670 | 11/2000 |
| WO | WO 01/08595 A1 | 2/2001 |
| WO | WO 01/15629 A1 | 3/2001 |
| WO | WO 01/21100 A1 | 3/2001 |
| WO | WO 01/21246 A1 | 3/2001 |
| WO | WO 01/89413 A2 | 11/2001 |
| WO | WO 02/43595 A2 | 6/2002 |
| WO | WO 02/054988 A2 | 7/2002 |
| WO | WO 02/094111 A2 | 11/2002 |
| WO | WO 2004/066826 A2 | 8/2004 |
| WO | WO 2004/066826 A3 | 8/2004 |
| WO | WO 2004/069098 A2 | 8/2004 |
| WO | WO 2004/069098 A3 | 8/2004 |

OTHER PUBLICATIONS

Search Report for International Application No. PCT/US2004/002756 (3 pages).
Search Report for International Application No. PCT/US2004/002757.
U.S. Appl. No. 11/704,076, filed Feb. 8, 2007 (62 pages).
Jun. 10, 2005 PCT International Search Report in International Application No. PCT/US2004/002756 (15 pages).
Sep. 8, 2004 PCT International Search Report in International Application No. PCT/US2004/002587 (17 pages).
US 6,348,062, 02/2002, Hopkins et al. (withdrawn)
US 6,461,371, 10/2002, McInnes (withdrawn)

* cited by examiner

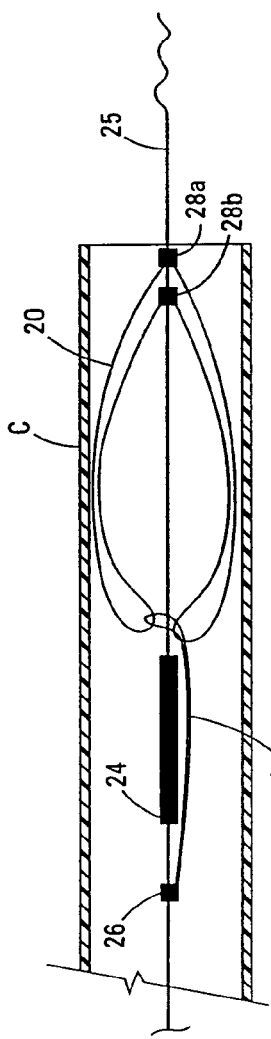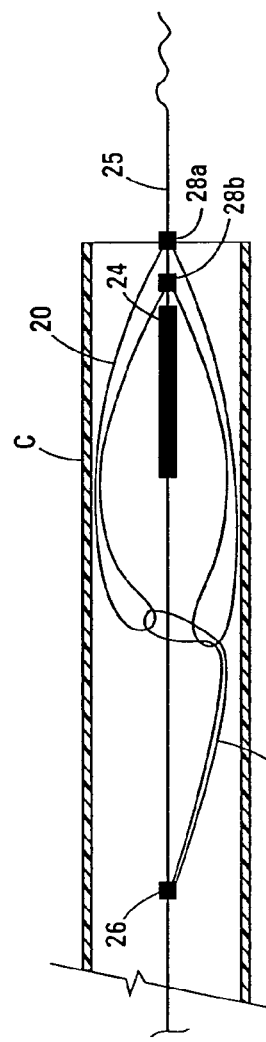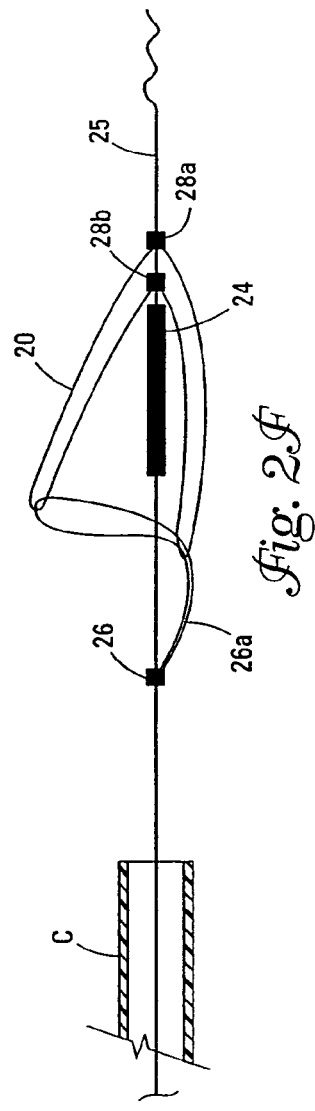

EMBOLIC FILTERS HAVING MULTIPLE LAYERS AND CONTROLLED PORE SIZE

CROSS-REFERENCE TO RELATED APPLICATION

This Application is a continuation of application Ser. No. 10/354,829, filed Jan. 30, 2003, now U.S. Pat. No. 7,220,271 B2, issued May 22, 2007, the contents of which are hereby incorporated herein by reference.

FIELD OF THE INVENTION

This invention relates to devices used in a blood vessel or other lumen in a patient's body. In particular, the present invention relates to devices for capturing emboli and particulate in a lumen.

BACKGROUND OF THE INVENTION

During vascular surgery or endovascular treatment of vessels including thrombectomy, atherectomy, balloon angioplasty, and/or stent deployment, debris such as plaque and blood clots can move from the treatment site through a vein or artery and compromise the flow of blood at a location removed from the treatment site. In particular, various protection systems have been developed to prevent such debris from embolizing in the vessel. Distal protection devices include filters and occlusive devices (e.g., balloons) placed distally of the treatment site. Proximal protection devices include filters and occlusive devices placed proximally of the treatment site. In the case of filters, emboli collect within or on the filter. The filter with captured emboli is typically collapsed into a recovery catheter and the catheter withdrawn from the patient's body.

The size or number of emboli that must be retained by the filter in order to prevent clinically undesirable sequaelae is unknown. This uncertainty adds to the complexity of designing a filter with the appropriate characteristics. Small particles might pass through the filter pores and lodge downstream in tissues where they may cause tissue ischemia or tissue necrosis. In the heart, blood can be drawn and measurements can be made to track enzyme levels and determine myocardial damage. However, in the brain there is no easy and inexpensive method to evaluate the effect of a shower of emboli. Within the downstream tissue bed, there is a statistical component to the consequences of an embolus. For example, a 100 micron particle may lodge in a part of the brain where few adverse consequences are detected clinically, or it can lodge in a retinal artery, resulting in blindness in one eye. Therefore, it may be necessary to adjust the filter characteristics to suit the region of emboli filtration. A smaller pore size filter may be needed if protecting the brain than protecting the heart or kidney.

Embolic protection filters permit the passage of blood while retaining emboli that are larger than the pore size of the filter. Filter meshes are commonly made by incorporating holes in a polymer film, by interweaving filaments, or by producing interconnected porosity in a sheet of material (e.g., foam). It is difficult to make an embolic protection filter with the appropriate combination of pore size, pore area, embolic capacity, patency, mechanical strength, low collapsed or retracted profile, and recovery characteristics. Embolic filters made from polymer films commonly have a narrow range of pore sizes but suffer from a low percent open area because there is a limit to how closely the holes can be placed. Too little spacing between holes can result in a weak film that tears upon filter recovery. Foams tend to be bulky, thereby compromising the collapsed profile, and they have low strength.

Interwoven meshes such as braids have the advantage of a pore area which is a high percentage of the total mesh area, excellent strength, and good flexibility, but tend to be made and used in ways that result in a wide range of pore sizes. A wide range of pore sizes is undesirable for a number of reasons. Patency is influenced by pore size. Theoretically, blood can be sheared as it flows through the pore, particularly at the edges of the pore opening. Shearing of blood can activate platelets and initiate a cascade of events that cause blood clotting. When filters are used in the bloodstream, it is common for thrombus to form in the vicinity of the smallest pores and no thrombus to form in the vicinity of the largest pores. Flow through the filter is thereby reduced because part of the filter becomes occluded. In addition, while some filters have a reasonable average pore size, a wide range of pore sizes in these filters may allow large particles to pass through the large pores during either the capture or recovery phase.

A need in the art remains for an embolic protection filter having pores which are both small in size and which do not vary in size beyond an acceptable range.

SUMMARY OF THE INVENTION

The invention provides an embolic filter that is designed to provide the desired characteristics of controlled pore size, high percentage of pore area, high embolic capacity, patency, mechanical strength, low collapsed or retracted profile, and strength during recovery.

It is to be understood that both the foregoing general description and the following detailed description are exemplary and explanatory and are intended to provide further explanation of the invention as claimed.

BRIEF DESCRIPTION OF THE DRAWINGS

FIGS. 2D to 2F are illustrative views showing deployment of a filter having a rolled back design.

DETAILED DESCRIPTION OF THE PREFERRED EMBODIMENTS

Figure 1A:
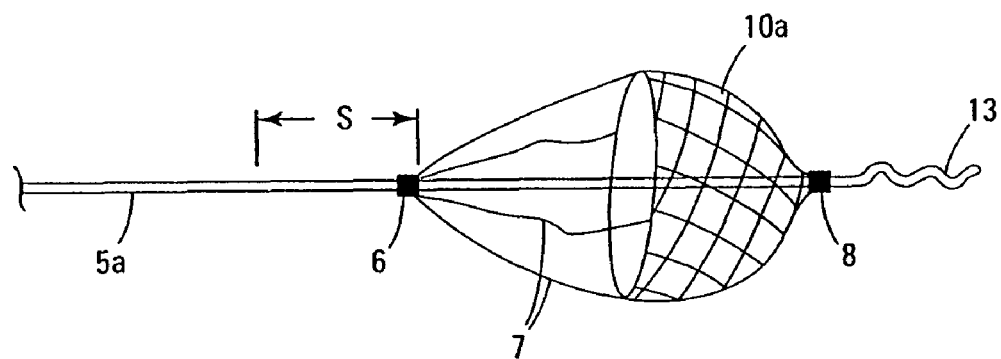
FIGS. 1A and 1B are schematic views of a distal protection system, illustrating expanded and contracted configurations, respectively, of a cup-shaped filter.

The terms "distal" and "proximal" as used herein refer to the relative position of the guidewire, catheters, and filter in a lumen. Thus, "proximal" refers to a location upstream from the "distal" position. That is, the flow of a body fluid, such as blood, moves from the proximal to the distal portions of the device.

The invention encompasses the use of any filtration device to be deployed in a lumen or vessel of a patient. Although the examples relate generally to filter protection devices deployed distal to a treatment site, the device can also be deployed proximal to a treatment site in connection with interrupting or reversing flow through the vessel. In the case of a proximally deployed device, it will be advantageous to construct the device on a hollow elongate member so as to preserve access to the treatment site through the hollow member.

In a preferred embodiment, the distal protection system comprises a catheter which is loaded with an elongate support member or guidewire about which is disposed a distal protection filter. The elongate support member is structurally similar to a traditional guidewire in some respects. However, it is not used as a means of navigating the patient's vascular system and, therefore, does not need to be provided with all of the features of flexibility and steerability as does a traditional guidewire. With these differences in mind, the terms elongate support member and guidewire may be used interchangeably herein. A floppy tip (described further below) may be at the distal end of the elongate support member or guidewire. Typically, the filter is introduced into a blood vessel through an introducing catheter. Methods of introducing guidewires and catheters and the methods for the removal of such devices from vessels are well known in the art of endovascular procedures. In a typical procedure using the device of this invention, the elongate support member and filter are loaded into an introducing sheath or catheter and moved into the vessel and through the catheter to the treatment site. This is done typically by advancing a first, or introduction guidewire, through the vessel to the region of interest. A catheter is advanced over the guidewire to the region of interest, and the guidewire removed. Then the filter or other functional device carried by the elongate support member is advanced down a catheter sheath to the region of interest but within the catheter. The catheter sheath is withdrawn to deploy (expand) the filter at the region of interest. Alternatively, the filter is preloaded into a catheter and held in place by an outer sheath of the catheter and they are together advanced through the vessel to the region of interest without using an initial guidewire. In this embodiment the catheter/filter combination will be used to navigate through the vessel to the region of interest. Then the catheter is withdrawn to deploy the filter. In a second alternative, an introduction guidewire is advanced to the region of interest, and the filter (contained in a catheter) is advanced over the guidewire to the region of interest, at which point the catheter is removed leaving the deployed filter near the region of interest on the guidewire. In this embodiment the filter is not comprised of an elongate support member as previously defined, and the guidewire and/or filter may be configured to preserve a spatial relationship between the guidewire and the filter. For example, the guidewire may be configured to prevent the filter from advancing beyond the distal end of the guidewire.

In other embodiments of the invention, no catheter is required for filter delivery. For example, the filter may be stretched axially so as to reduce its diameter to a size suitable for navigation through a vessel and across a treatment site.

In some embodiments of the invention, the device can include an actuator instead of being self-expanding. Actuators include struts, coaxial elongate elements, expandable elements such as balloons, support frames, etc.

Typical dimensions of a filter used in the devices of this invention range from 2 mm to 90 mm in length, and from about 0.5 mm to 2 mm in diameter before deployment, and from about 2 mm to 30 mm in diameter after deployment. A typical guidewire is about 0.2 to 1.0 mm in diameter and ranges from 50 cm to 320 cm in length.

The components of the distal protection system are made from biocompatible materials. Materials also may be surface treated to produce biocompatibility. The elongate support member may be formed of any material of suitable dimension, and generally comprises metal wire. Suitable materials include stainless steel, titanium and its alloys, cobalt-chromium-nickel-molybdenum-iron alloy (commercially available under the trade designation ELGILOY™), carbon fiber and its composites, and engineered polymers such as liquid crystal polymers, polyetheretherketone (PEEK), polyimide, polyester, and the like. A shape memory or superelastic metal such as nitinol is also suitable. The elongate support member may be solid or may be hollow over some or all of its length.

The material used to make the filter or filter support structure is preferably self-expanding. Suitable materials include metals such as stainless steel, titanium and its alloys, cobalt-chromium-nickel-molybdenum-iron alloy (commercially available under the trade designation ELGILOY™), carbon fiber and its composites, and engineered polymers such as liquid crystal polymers, polyetheretherketone (PEEK), polyimide, polyester, silk, and the like. A shape memory or superelastic metal is particularly suitable for those applications when it is desired for an element, such as a filter, to assume a pre-determined three-dimensional shape or for a guidewire to maintain a pre-determined curvature. A shape memory or superelastic metal comprising nickel and titanium known as "nitinol" is commercially available in various dimensions and is suitable for use as both a guidewire and a filter. For example, nitinol tubular braid can be heat set into a desired shape, compressed for delivery to a site, and then released to resume the heat-set shape.

The filter element has a body defining an interior cavity. The filter body has a plurality of openings or pores such that, when the filter element is in its deployed configuration within the vessel lumen, fluid flows through the filter element and particles of the desired size are captured inside the interior cavity of the filter element.

The filter may comprise any material that is suitably flexible and resilient, such as a mesh, i.e., a material having openings or pores. The filter may comprise braided, knitted, woven, or non-woven fabrics that are capable of filtering particles, preferably having pore sizes from 30 to 500 microns. Woven or non-woven fabrics may additionally be treated to fuse some or all of the fiber intersections. The fabric may be spun or electrospun. Suitable materials include those formed from sheets, films, or sponges, polymeric or metallic, with holes formed by mechanical means such as laser drilling and punching, or by chemical means such as selective dissolution of one or more components. For example, a suitable filter material is braided tubular fabric comprising superelastic nitinol metal. Mesh fabric of nitinol material can be heat-set to a desired shape in its expanded configuration.

The material comprising the filter is preferably at least partially radiopaque. This material can be made radiopaque by plating, or by using core wires, tracer wires, or fillers that have good X-ray absorption characteristics compared to the human body. Radiopaque filters are described in U.S. patent application Ser. No. 10/165,803, filed Jun. 7, 2002, entitled "Radiopaque Distal Embolic Protection Device," the contents of which are hereby incorporated by reference herein.

The embodiments of this invention, described in detail below in connection with the figures, are suitable for use with various distal protection systems that are known in the art. The filter may have a windsock type shape. The construction, deployment and retrieval of a filter having this shape is described, for example, in U.S. Pat. No. 6,325,815 B1 (Kusleika et al.), the contents of which are hereby incorporated by reference herein.

The filter may also be a cup-shaped or basket-shaped device which forms a proximally facing opening when expanded. The construction, deployment, and retrieval of such a filter is described in WO 96/01591 (Mazzocchi et al.). This cup-shaped device may generally resemble an umbrella or a parachute, having a dome-like structure curving radially outwardly from the guidewire or elongate support member. Other shapes may be equally suitable in performing a filtering function, such as a conical shape, or a relatively flat disc shape. The filter may include a filter basket having a self-expanding radial loop designed to position the filter basket within the vasculature and to hold the filter basket open during deployment. Such a filter is described in EP 1 181 900 A2 (Oslund et al.). It will be appreciated that the shape of these filtration devices shown in various embodiments are merely illustrative and are not meant to limit the scope of the invention.

Regardless of the shape of the filter, the filter preferably is deployed using an elongate support member. This can be done in various ways, and one or both of the proximal and distal ends of the filter may be affixed to the elongate support member (by a fixed element) or may be slidably disposed about the elongate support member (by one or more sliding elements).

One type of sliding element comprises inner and outer annular rings. The first ring fits within the second ring. The inner diameter of the first ring is larger than the diameter of the elongate support member so that the sliding element can slide over the elongate support member. The sliding element can be affixed to the filter fabric by placing the fabric between the first and second rings. However, this is not meant to be limiting, and the filter fabric can also be affixed to the sliding element by adhesive, solder, crimping, or other means known in the art. The sliding element may comprise any stiff material such as metal or polymer and preferably the slider is radiopaque. Suitable materials include stainless steel, titanium, platinum, platinum/iridium alloy, gold alloy, polyimide, polyester, polyetheretherketone (PEEK), and the like. Movement of a sliding element with respect to the elongate support member can be facilitated by coating one or both of the inside of the sliding element and the outside of the elongate support member with a friction-reducing coating, such as polytetrafluoroethylene or a lubricious hydrophilic coating.

Fixed elements include annular rings. Also included within this meaning is an element that is crimped, adhered, soldered, or otherwise fastened directly to the elongate support member. Also, the filter fabric may be attached directly to the elongate support member. In any event, the sliding and fixed elements (or any attachment point) typically comprise radiopaque material to assist in the placement of the filter. In addition, one or more radiopaque markers may be positioned at various locations on the protection device. These radiopaque markers or marker bands comprise a material that will be visible to X-rays and they assist in positioning the device.

Some distal protection filters include a floppy tip at a distal portion of the guidewire or elongate support element. The floppy tip provides an atraumatic and radiopaque terminus for the device. An atraumatic tip prevents vessel injury during initial placement or subsequent advancement of the device. A radiopaque tip helps the physician verify suitable tip placement during fluoroscopy. The floppy tip preferably comprises a springy or resilient material, such as a metal (e.g., stainless steel, iron alloys such as ELGILOY™, platinum, gold, tungsten, and shape memory or superelastic metal such as nitinol) or polymer (e.g., polyetheretherketone (PEEK), polyimide, polyester, polytetrafluoroethylene (PTFE), and the like). Springy materials are desirable because they tend to retain their shape. The physician will initially shape the tip, typically with a slight curve, and then as the device is advanced through the body the tip will be deflected as it encounters obstacles. It is desirable, after the inevitable deflections during insertion, that the tip restore itself to the pre-set shape. Polymeric materials additionally may be reinforced with metals or other fillers. The tip may be a monofilament or multifilament (such as a cable). The floppy tip may be tapered or have a uniform diameter over its length. The floppy tip may comprise a tube, or could have circular, flat, or other cross-sections. It may be coiled. The tip may comprise one or more elements (for example, parallel independent structures). The tip may be polymer-coated or otherwise treated to make the surface slippery. The floppy tip can be any desired length.

The filter comprises biocompatible materials such as metals and polymeric materials. Materials such as metals and polymeric materials can be treated to impart biocompatibility by various surface treatments, as known in the art. When wire is used, the wire is selected on the basis of the characteristic desired, i.e., stiffness or flexibility, and the properties can depend upon both the diameter of the wire and its cross-sectional shape. The size, thickness, and composition of elastic materials are selected for their ability to perform as desired as well as their biocompatibility. It is to be understood that these design elements are known to one of skill in the art.

Filters are typically constructed as described in U.S. Pat. No. 6,325,815 B1. See column 3, line 63, to column 4, line 16; and column 4, line 48, to column 5, line 36. The filter body typically comprises a length of a braided tubular fabric, preferably made of nitinol. The filter body is typically made by placing a braided tubular fabric in contact with a molding surface of a molding element which defines the shape of the desired filter body. By heat treating the braided tubular fabric in contact with the molding surface of the molding element, one can create a filter body having virtually any desired shape.

Braiding is a process for producing a tubular interwoven structure from individual strands. Braids are typically produced in continuous lengths on commercially available braiding machines. Some commercial products produced on braiding machines include rope, shoelaces, and reinforcing jackets for electrical cable. Medical products produced by braiding include stents, vascular grafts, and catheter reinforcing layers.

In a typical braiding process for making a 72 stranded braid, lengths of strands, such as wire, are wound onto bobbins. In this example 72 bobbins are wound with wire. Each bobbin is loaded into the carrier of a 72 carrier braiding machine. Typically braiding machines for medical use have from 16 to 144 carriers or more. Each wire is led through a tensioning mechanism in the carrier and all wire strands are gathered at a common central elevated position along the (typically vertical) axis of the braiding machine, where they are fastened to a take-up mechanism. The take-up mechanism may be a long mandrel arranged along the axis of the braiding machine and onto which the braid is formed during the braiding process. Once so configured, the carriers are rotated relative to the axis of the braiding machine. The carriers are rotated in a serpentine path, half of them moving clockwise and the other half moving counterclockwise, so as to interweave the strands in a programmed pattern. While the carriers are rotating, the take-up mechanism advances the woven braid in a direction away from the carriers. The combination of these motions produces a helix of strands twisting in a clockwise direction along the mandrel, interwoven with a helix of strands twisting in a counterclockwise direction along the mandrel. In this manner continuous lengths of braid are produced with an inside diameter of the braid equal to the outside diameter of the braiding mandrel. The individual braid strands, while still on the mandrel, can be twisted together after the length of the mandrel has been braided. If desired, after removing the mandrel from the braiding machine, the strands can be heat-treated. In the case of nitinol strands, heat treatment on the mandrel at about 525° C. for 10 minutes or so can cause the nitinol-braided fabric to remember the shape and size of the mandrel when the nitinol is at rest.

The average pore sizes of filters of the invention preferably range from 30 to 300 microns. In another preferred embodiment, the average pore sizes range from 30 to 150 microns. A pore size of about 120 microns is preferred for devices intended to be used in connection with coronary procedures and a pore size of about 50 microns is preferred for devices intended to be used in connection with carotid or intracranial procedures. The variation in pore size within the filter should be minimized. In preferred embodiments of the invention, the standard deviation of the pore size is less than 20 percent of the average pore size. In other preferred embodiments, the standard deviation of the pore size is less than 15, 10, 5, or 2 percent of the average pore size.

The percent open area of the filters of the invention is preferably greater than 50 percent. In other preferred embodiments, the percent open area is greater than 60, 70, or 80 percent. A standard formula is used to calculate the percent open area of a given design. The percent open area is calculated by dividing the total pore area by the total filter area (including the pore area).

The filters of the invention preferably are made of a material having a tensile strength of greater than 70,000 psi (7031 kg/cm$^2$), more preferably greater than 150,000 psi (14,062 kg/cm$^2$), and more preferably greater than 200,000 psi (17, 578 kg/cm$^2$). Cast polymer films have a maximum tensile strength of about 10,000 psi (703 kg/cm$^2$); oriented polymer films have a tensile strength as high as 50,000 psi (3516 kg/cm$^2$), and metal filters typically contain wires having a tensile strength of from 70,000 to 300,000 psi (7031 kg/cm$^2$ to 21,093 kg/cm$^2$).

The various embodiments of the invention will now be described in connection with the drawing figures. It should be understood that for purposes of better describing the invention, the drawings have not been made to scale. Further, some of the figures include enlarged or distorted portions for the purpose of showing features that would not otherwise be apparent. The material comprising the filter (e.g., mesh or fabric with pores, as described above) is indicated by cross-hatching in some of the figures but is omitted from others for simplicity.

Figure 1B:
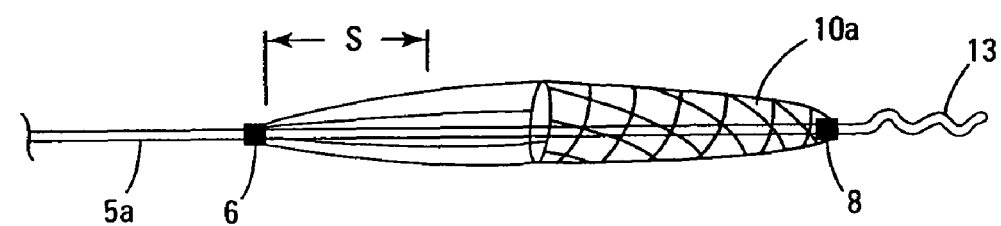
Figure 1C:
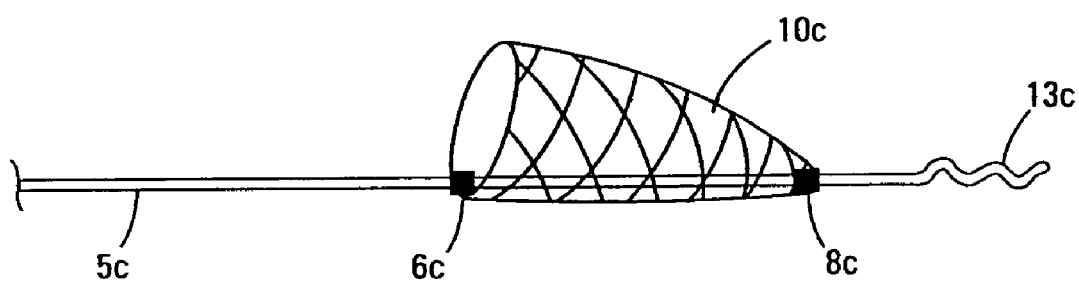
FIG. 1C is a schematic view of an alternative distal protection system having a windsock-shaped filter.

FIGS. 1A, 1B, and 1C illustrate embodiments of single layer filters. The concepts of the present invention relating to multiple layer filters can be applied to the types of filters shown in FIG. 1. The application of these concepts is not, however, limited to these embodiments and are equally applicable for use in any filter where control of pore size is desirable. FIGS. 1A and 1B illustrate schematic views of a distal protection system in which elongate support member 5a carries filter 10a. The proximal end of the filter is connected to a proximal sliding element 6 and the distal end of the filter is connected to a distal fixed element 8. The distal fixed element is connected at a fixed location on the elongate support member while the proximal slider is configured to slide freely over the elongate support member. Struts or tethers 7 attach to the body of the filter and to sliding element 6. The elongate support member terminates distally at optional atraumatic floppy tip 13. The filter is shown in its expanded deployed configuration in FIG. 1A and in its contracted delivery configuration in FIG. 1B. The figures show that the proximal sliding element 6 travels over the elongate support member a distance S when the filter is contracted to, for example, its delivery configuration.

FIG. 1C illustrates another type of distal protection system in which windsock-shaped filter 10c is attached to elongate support member 5c which terminates at floppy tip 13c. The filter is attached to support member 5c via proximal element 6c and distal element 8c. Either one or both of these elements may be sliding or fixed elements, as described above.

It is to be understood that the following embodiments are useful for any shape or type of filter. For example, these embodiments are useful for any filter deliverable by any manner to a desired position in a body lumen where control of the desired characteristics of the filter as set forth above is desired. In particular, the invention includes both proximal and distal filters.

Rolled Back Filters

Figure 2A:
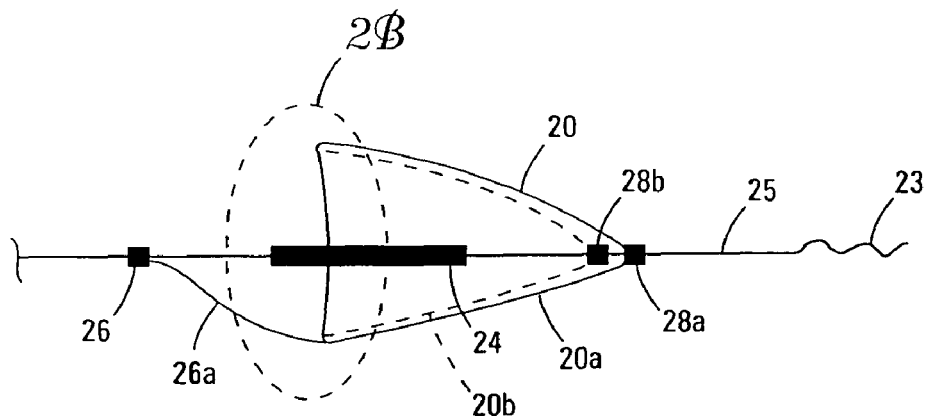
FIGS. 2A to 2C are side views of various embodiments of a filter having a rolled back design.
Figure 2B:
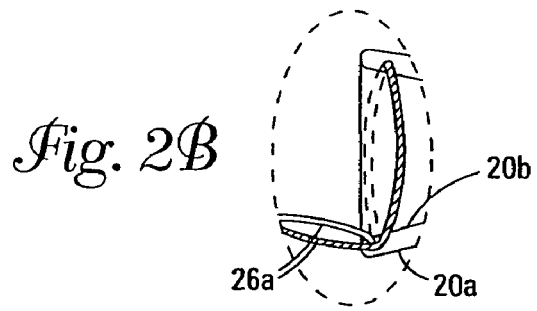

FIGS. 2A to 2F illustrate rolled back filter designs. These drawings show a windsock-shaped filter. The filters comprise a mesh such as a braided shape memory metal formed so that the mesh rolls back on itself, forming two mesh layers. FIG. 2A illustrates such a system in cross section, wherein filter 20, comprising layers 20a and 20b, is mounted to elongate support member 25 via distal sliding element 28a (for the outer filter layer 20a) and 28b (for the inner filter layer 20b). The elongate support member terminates distally at floppy tip 23. The proximal end of filter 20 is attached to a proximal sliding element 26 by means of tether 26a. FIG. 2B illustrates an enlarged view of the tether 26a and filter 20. Stop 24 prevents excessive support member motion relative to the filter. In this design the sliding elements typically are cylindrical marker bands comprising radiopaque material. Stop 24 is a cylinder bonded to the elongate support member. The stop may be rigid or flexible, such as for example a hypotube, a wound coil, a spirally cut hypotube, a slotted hypotube, a polymer elastomeric tube, and the like. Tether 26a typically is a flexible wire loop, such as nitinol, that loops from the proximal sliding element 26, through the mesh of the filter or between the braid layers or a combination of through the mesh and between the layers, and back to the sliding element. The tether can be made of metal or polymer, can be monofilament, yarn, stranded, or cabled. Preferably the tether enters and exits the mesh at substantially the same location so that the tether can function as a drawstring when recovering the filter. The double layer mesh functions to reduce the pore size of the filter versus that of a single layer filter. For example, if the two layers of mesh are properly aligned and in substantial contact with each other, the filter pore size will be approximately half of the pore size of a single layer of mesh. The filter may have memory imparted to the rolled over region, as discussed below in connection with FIGS. 13A and 13B, or may contain a rivet or joining component as discussed below in connection with FIGS. 15 to 18.

Figure 2C:
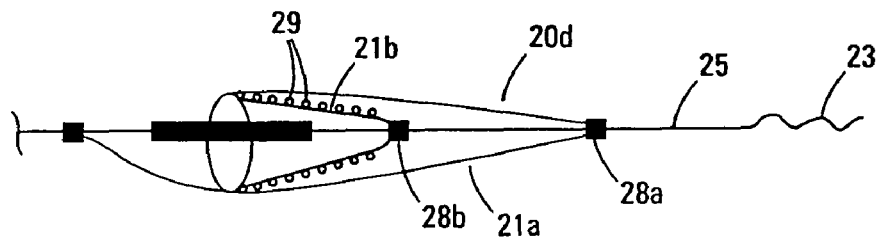

FIG. 2C illustrates another variation of this filter 20d, in which inner filter portion 21b is wrapped with polymer filaments 29. These filaments may be wrapped in a spiral configuration. Alternatively, inner filter portion 21b could be wrapped with braid or a thin sheet of plastic with drilled holes. The wrappings may be joined to the inner filter portion using techniques discussed in connection with FIGS. 15 to 18. Importantly, the wrapping preferably is entirely contained within the filter 20d and cannot pass into a vessel even if the wrappings become disconnected from the inner filter 21b. These wrappings reduce the effective pore size of the filter by occluding or partially obstructing pores in the mesh.

FIGS. 2D to 2F illustrate the delivery of a rolled back filter. Filter 20, attached to elongate support member 25, is loaded into catheter C in a collapsed position. This is accomplished by withdrawing elongate support member 25 into catheter C, which causes stop 24 to contact proximal sliding element 26, further causing tether 26a to collapse and withdraw filter 20 into catheter C.

After advancing catheter C to a region of interest, typically downstream of a stenosis in a vessel such as an artery, the filter is deployed. Filter deployment can be achieved by advancing elongate member 25 distally with respect to catheter C. Said relative movement will cause stop 24 to contact distal slider 28b, and further motion will move slider 28b distally with respect to catheter C until the filter 20 exits catheter C and expands within the region of interest or vessel. Distal slider 28b may contact distal slider 28a during deployment of the filter. At this point elongate support member 25 can move proximally and distally a limited distance without disturbing filter 20.

After filter 20 has captured embolic debris or after the region of interest has been treated or diagnosed, filter 20 may be recovered into a catheter, which may or may not be the same catheter as that used to deliver the filter, treat the patient, or diagnose the patient, by withdrawing the elongate support of member into the catheter in a manner similar to that described above.

Insert Filters

Figure 3A:
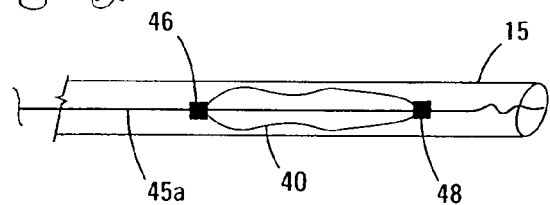
FIGS. 3A to 3E are illustrative views showing deployment of a second filter within a first filter.
Figure 3B:
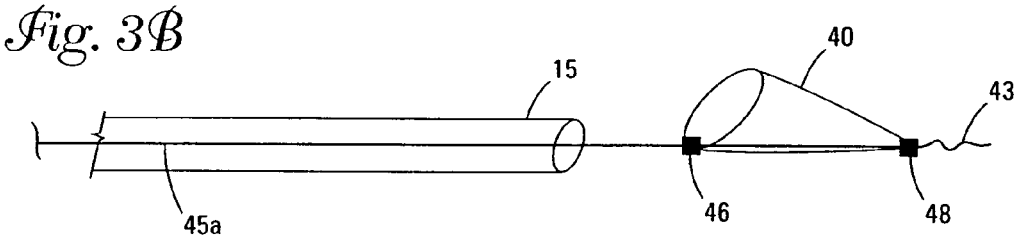
Figure 3C:
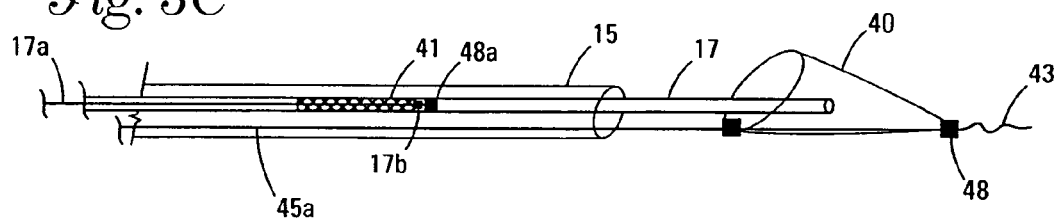
Figure 3D:
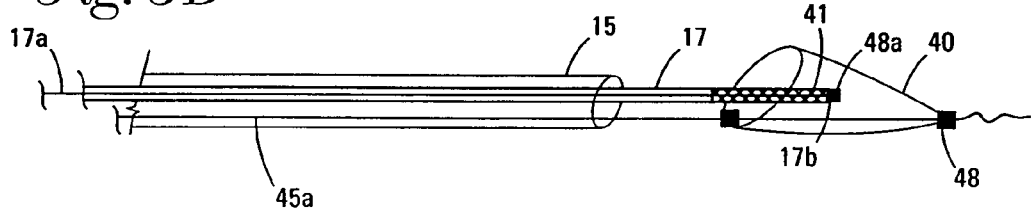
Figure 3E:
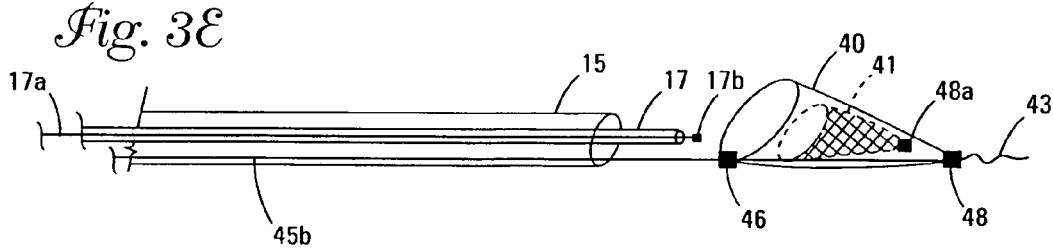

FIGS. 3A to 3E illustrate the delivery and deployment of another type of filter construction. As shown in FIG. 3A, first, or outer filter 40 is placed in delivery catheter 15. Filter 40 is mounted on elongate support member 45a and has distal and proximal sliding elements 46 and 48, respectively. Support member 45a may contain a stop similar to that described in connection with FIG. 2 (not shown in the FIGS. 3A to 3E, for clarity) and terminates distally at floppy tip 43. Filter 40 is moved distally, out of the catheter, and deployed in FIG. 3B. FIG. 3C shows second delivery catheter 17 inside first catheter 15 extending to the inside of filter 40. Catheter 17 contains second filter 41, having distal element 48a which holds together individual strands of the mesh of second filter 41. Second filter 41 is moved through catheter 17 by pusher element 17a. Pusher element 17a has a distal enlargement 17b, such as a ball, that engages the interior of second filter 41 but is prevented from passing distally through filter 41 by element 48a. Filter 41 is placed within first filter 40 by advancing second catheter 17 distally within filter 40, advancing pusher element distal enlargement 17b distally against element 48a, and withdrawing catheter 17 proximally relative to pusher 17a. After filter 41 exits catheter 17, pusher 17a, catheter 17, and catheter 15 are withdrawn. In a preferred embodiment, the second filter has a smaller average pore size than the first filter. An advantage of this design is that the two filters can have different constructions, pore sizes, and characteristics. A further advantage of this design is that the filter mass can be stretched out over a longer length of delivery catheter, thereby permitting the delivery catheter profile to be reduced. Low profile delivery catheters typically are more flexible, have better tracking characteristics, and have better lesion crossing characteristics.

Figure 4A:
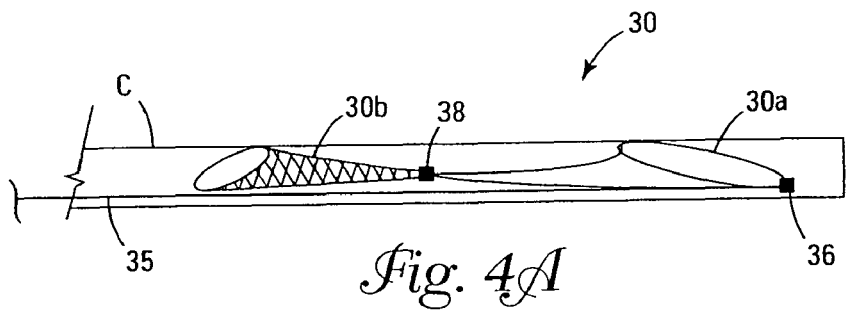
FIGS. 4A to 4D are side views illustrating the formation of a second filter within a first filter.
Figure 4B:
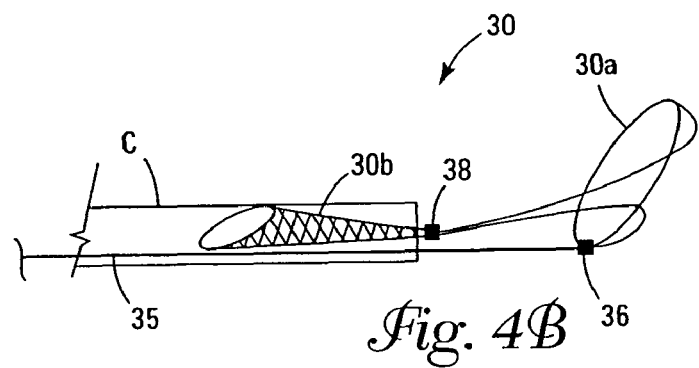
Figure 4C:
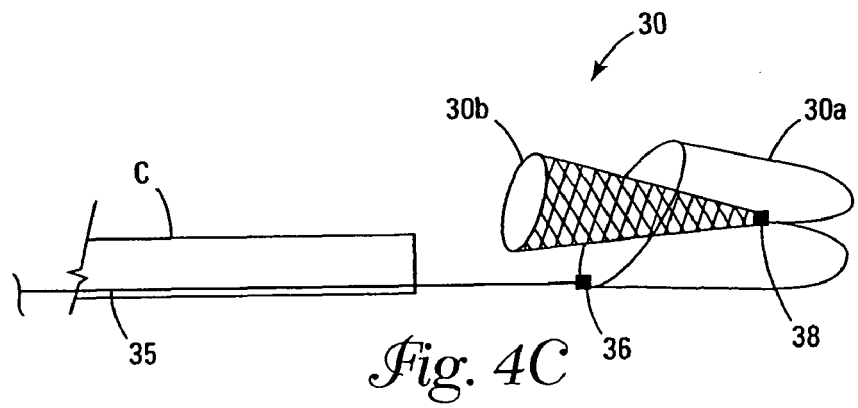
Figure 4D:
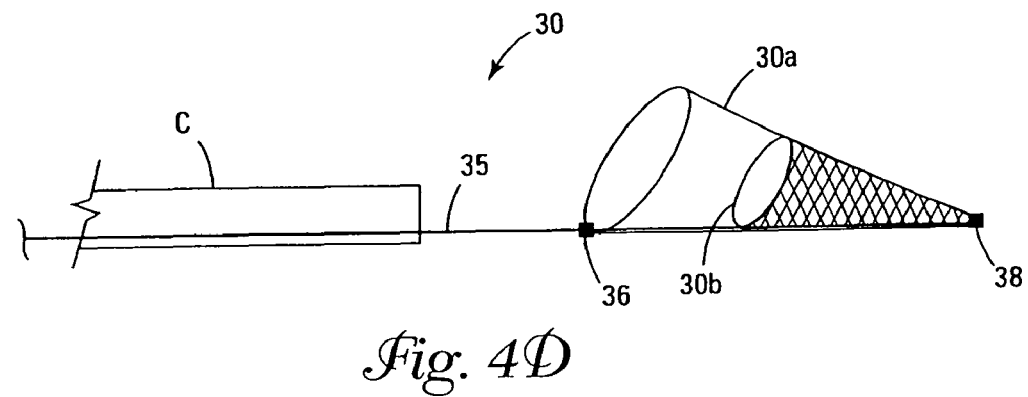
Figure 5A:
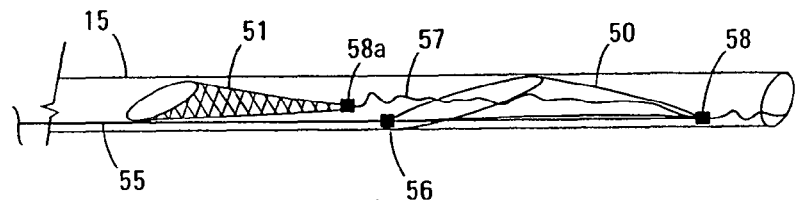
FIGS. 5A to 5D are illustrative views showing deployment of a second filter within a first filter.
Figure 5B:
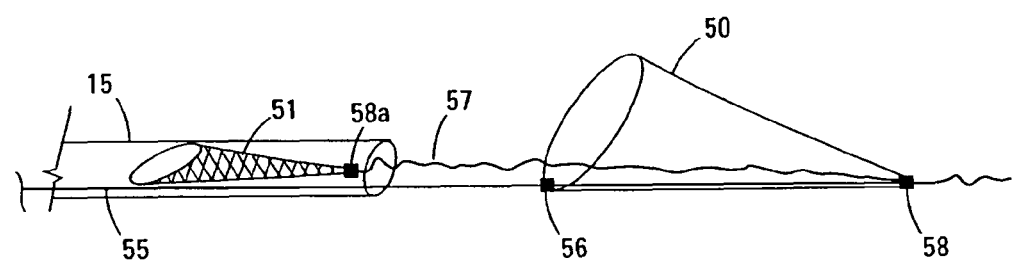
Figure 5C:
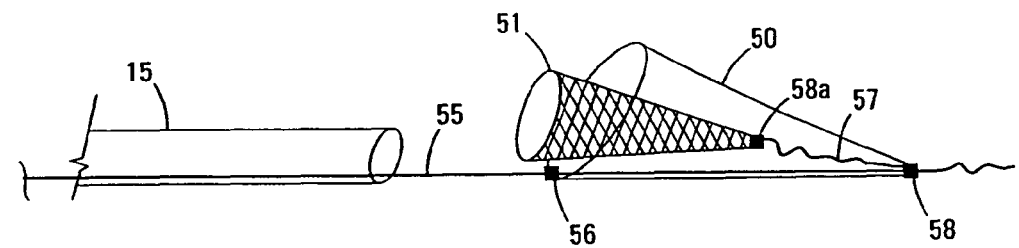
Figure 5D:
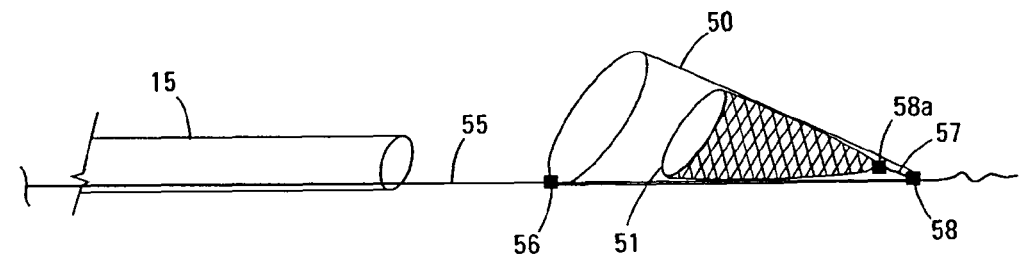

FIGS. 4A to 4D illustrate an alternative construction of an insert filter with similarities to that shown in FIGS. 3A to 3E. Filter 30, attached to elongate member 35, is loaded within catheter C. Filter 30, comprised of outer mesh portion 30a and inner mesh portion 30b, is loaded into catheter C in a radially collapsed position. Preferably inner mesh portion 30b is of a finer pore size than outer mesh portion 30a. Both portions may be comprised of braid, preferably a nitinol self-expanding braid. Filter 30 is pre-programmed to assume the configuration shown in FIG. 4D, and is loaded into catheter C by grasping the opening of inner mesh 30b and holding onto it while advancing the distal end of elongate member 35 into the proximal end of catheter C. Band 38 is similar to fixed elements discussed earlier and may be a marker band which compresses mesh at the junction of mesh portions 30a and 30b. Fixed element 36 is similar to those described earlier and may be a metallic radiopaque band which attaches mesh portion 30a to elongate member 35. After loading into catheter C, filter 30 may be deployed after catheter advancement to a region of interest by withdrawing catheter C relative to filter 30. As catheter C is withdrawn, outer mesh portion 30a will begin to assume its pre-programmed shape as shown in FIG. 4B. Further withdrawal of catheter C will allow mesh portion 30b to exit the catheter and restore itself to the pre-programmed configuration shown in FIGS. 4C and 4D.

The design shown in FIGS. 4A to 4D has similarities to that shown in FIG. 3A to 3E in that the mass of the filter can be distributed over more catheter length (and thus the catheter can have a smaller diameter) yet also has the advantage of a more secure connection between the inner and outer mesh layers. The design shown in FIG. 4A to 4D is preferably self-expanding with sufficient pre-programmed restoring force to cause the device to self-restore to the shape shown in FIG. 4D in a vessel or a region of interest.

After use, filter 30 can be easily recovered by advancing a catheter, such as C, distally with respect to elongate support member 35 until fixed element 36 enters catheter C. At this point the mouth of mesh portion 30a will collapse into catheter C and the combination can be withdrawn from the patient. Alternatively, catheter C can be further advanced over filter 30 until some or all of the filter is within catheter C, and the catheter can then be withdrawn from the patient.

FIGS. 5A to 5D illustrate yet another embodiment of an insert filter, wherein the outer and inner mesh portions (50 and 51, respectively) are coupled together by coupling element 57. This coupling element may be an elastic or spring-like material, and may comprise nitinol, elastomers, coils, or other materials as known in the art. Outer portion 50 is mounted on elongate support member 55 by proximal and distal sliding elements 56 and 58 and contains a stop similar to that shown in FIG. 2 (not shown in FIG. 5 for clarity). Alternatively one of sliding elements 56 or 58 may be fixed, and the stop may be eliminated. Inner portion 51 terminates at distal fixed element 58a and coupling element 57 attaches to element 58a and element 58. The two portions are loaded into catheter 15 by front loading them into the proximal end of the catheter, and are advanced distally through catheter 15 in a low or compressed profile by pushing distally on elongate support member 55. First portion 50 is moved out of the catheter and deployed, as in FIG. 5B. As portion 50 is moved farther distally relative to catheter 15, portion 51 exits the catheter. Alternatively, catheter 15 may be withdrawn proximally relative to portion 50. Coupling element 57 pulls the inner portion 51 into the outer portion 50. Outer portion 50 may be mesh such as a nitinol braid element and the inner portion 51 is preferably a more densely braided, woven, or mesh filter, sized to be placed into the outer portion. In a preferred embodiment, the inner portion 51 has a smaller average pore size than the outer portion 50. Alternatively, the inner portion has large pores proximally and small pores distally while the outer portion has small pores proximally and large pores distally such that when the two filters are in contact the effective pore size is reduced as compared to either filter alone. It is preferred that the inner filter expands into close contact with the outer filter, most preferably such that the spacing between the two filters is about equal to the effective pore size of the overall filter, so that the two layers cooperate in the filtering function.

The filter of FIGS. 5A to 5D has the advantages of distributing the mass of the filter within the delivery catheter, secure connection between the filtering layers, controlled and uniform pore size, and easy recovery by withdrawing the elongate support member 55 into a catheter.

Figure 6A:
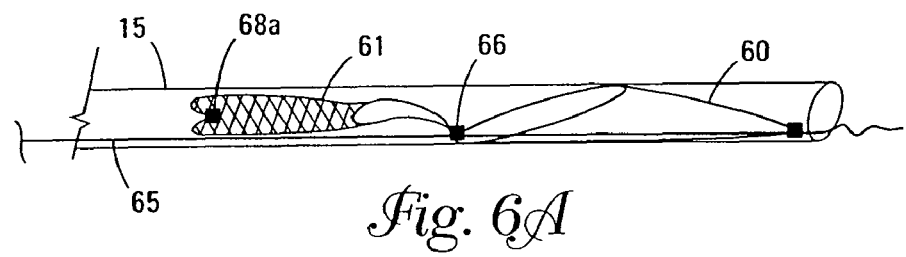
FIG. 6A is a side view showing the filters within a catheter in a delivery configuration.
Figure 6B:
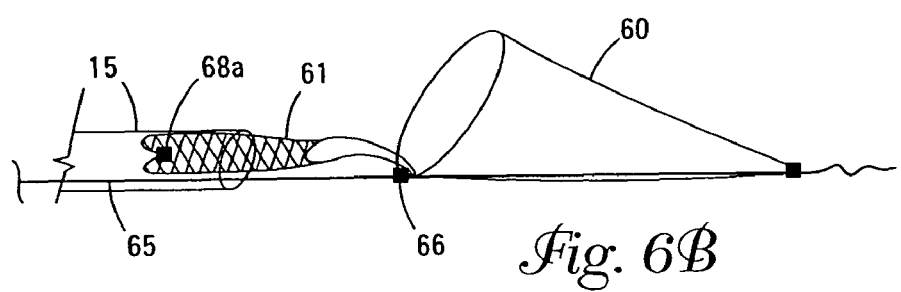
FIGS. 6B and 6C are side views showing a filter within a filter construction in delivery configurations.
Figure 6C:
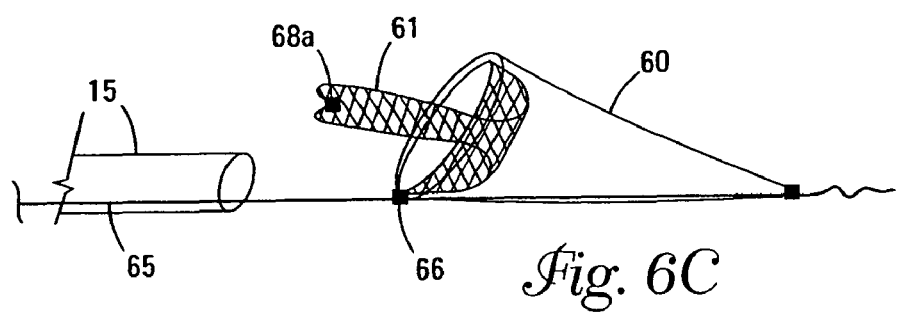
Figure 6D:
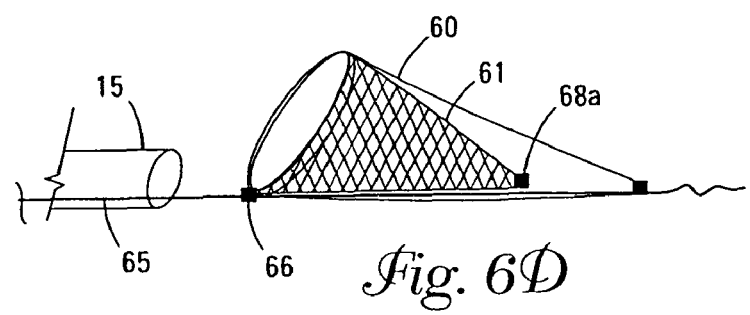
FIG. 6D is a side view showing the deployed configuration.

Another way to configure the geometry of the filtering layers is illustrated in FIGS. 6A to 6D. Outer portion 60 is mounted to elongate support member 65. Elongate support member 65 may contain a stop as described in connection with FIGS. 2A to 2F. The inner filter portion 61 is coupled to the outer filter portion 60 at the proximal element 66. Inner filter portion 61 is inverted relative to its service configuration (shown in FIG. 6D) and may attach to distal element 68a for the purpose of gathering and controlling mesh strands. Upon filter delivery, portion 61 inverts and fits inside filter 60. This may be accomplished by blood flow in a vessel, may be accomplished by use of a tether as described in connection with FIGS. 5A to 5D, may be accomplished by means of a pusher element as discussed in connection with FIGS. 3A to 3E, may be accomplished by a strongly set shape restoring force in filter 61, or other means. FIGS. 6B and 6C illustrate the configuration of the filter as it is being deployed, and FIG. 6D illustrates the configuration of the filter when deployed. Filter loading within the delivery catheter can be accomplished using methods similar to those discussed in connection with FIGS. 5A to 5D. As shown in FIG. 6A, an advantage of this design is that the bulk of the filter is reduced in the delivery catheter. In other designs the two filtering layers occupy the same cross sectional area of the delivery catheter, whereas in this design the mass of the filter is spread out over more catheter length. This permits smaller delivery catheter crossing profiles. Another advantage of this design is that filter layers 60 and 61 are securely attached to elongate support member 65 at proximal element 66, thereby assuring that during filter recovery the proximal openings of both filters can be drawn into a recovery catheter and closed to prevent escape of captured emboli through the proximal openings. In a preferred embodiment, the inner filter portion 61 has a smaller average pore size than the outer filter portion 60.

Figure 7A:
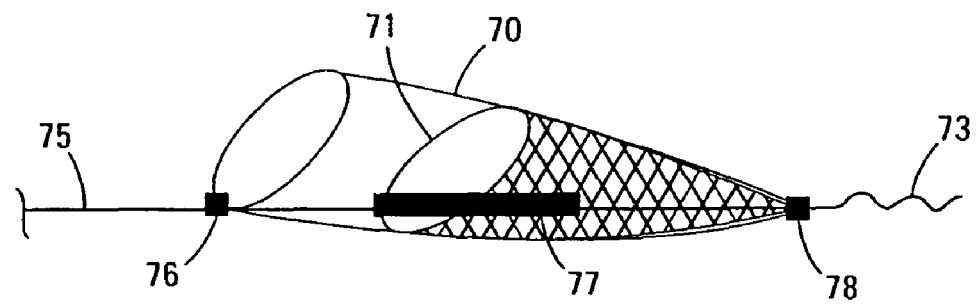
FIGS. 7A and 7B are side views showing a second filter within a first filter.

FIG. 7A illustrates an alternative configuration of filtering layers, in which inner filter portion 71 and outer filter portion 70 are both mounted on elongate support member 75 and both attach distally to distal element 78. Support member 75 terminates distally at floppy tip 73. Filter portion 70 also is affixed to proximal slider element 76. Stop 77 is also provided. In a preferred embodiment, a single layer of self-expanding mesh comprises inner filter portion 71 and is attached to the distal sliding element. Preferred materials for the inner mesh include high stiffness materials with high expansion force. Common biomedical materials such as nitinol, stainless steel, and ELGILOY™ are suitable. High modulus materials such as molybdenum, tungsten, osmium, niobium, and their alloys, are preferred since for a given diameter they can provide higher forces for filter expansion and shape retention. Proximal ends of inner filter portion 71 may be comprised of hooks as described in connection with FIGS. 14A to 14F, may be bonded to outer filter as described in connection with FIGS. 12A and 12B, or the layers may be joined using means such as those described in FIGS. 15 to 18. In a preferred embodiment, the mesh of filter portion 71 has a pore size smaller than that of the outer filter portion 70.

Figure 7B:
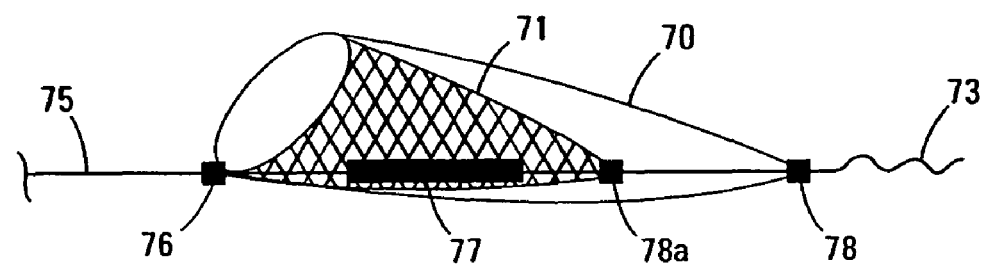

FIG. 7B illustrates another configuration, in which inner filter portion 71 attaches to or is integral with the proximal end of the outer filter portion 70. Both portions have distal sliding elements, shown at 78 and 78a. The filter is mounted on elongate support element 75 which may contain stop 77 and terminates distally at floppy tip 73. Inner and outer portions are attached to proximal sliding element 76. In a preferred embodiment, the inner filter portion 71 has a larger average pore size than the outer filter portion 70 so that the inner filter will remove large emboli from the flow stream before they reach the fine filter. This helps to keep the fine filter from becoming clogged with debris, as does the relatively larger overall area of the fine filter. This configuration also has the advantage that the inner and outer layers are inseparable at the proximal filter opening, which prevents emboli from bypassing the inner pre-filtering layer, and provides good recovery characteristics as described above in connection with FIG. 6.

Figure 8A:
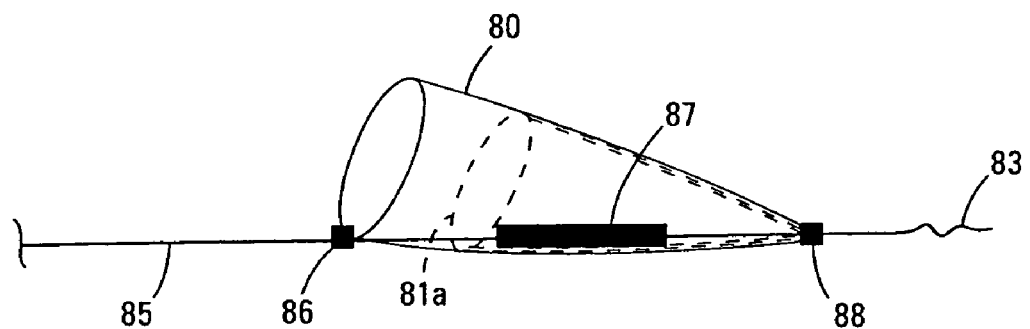
FIGS. 8A and 8B are side views of a rolled back second filter within a first filter.
Figure 8B:
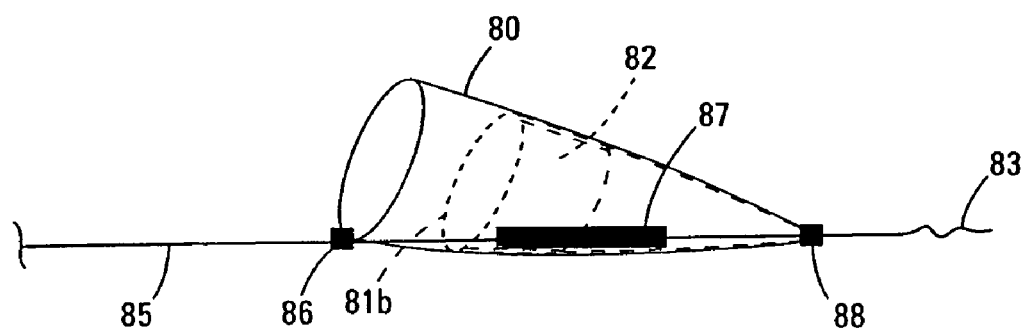

FIGS. 8A and 8B illustrate embodiments in which a rolled back configuration is used for the inner filter portion. FIG. 8A shows a rolled back material for inner filter portion 81a, comprised of one tubular layer rolled back over itself with both tubular ends attached to element 88. Both inner filter portion 81a and outer filter portion 80 are mounted on elongate support member 85 and both attach distally to distal element 88. Support member 85 terminates distally at floppy tip 83. Filter portion 80 also is affixed to proximal slider element 86. Stop 87 may be provided. Inner filter portion 81a is similar to filter 71 shown in FIG. 7A, for example, in which an outer mesh portion surrounds an inner mesh portion, however in FIG. 8A the filter is comprised of three layers rather than the two layers shown in FIG. 7A. Inner filter 81a may be joined, bonded, or connected to outer filter 80 as described in connection with FIG. 7A. FIG. 8B shows a filter similar to that of FIG. 8A, except that only a portion of the inner filter has two layers. Thus, FIG. 8B shows inner filter portion 81b having a rolled back portion 82 at its proximal end. In preferred embodiments, the inner filter portions have smaller average pore sizes than the outer filter portions. An advantage of using a rolled back inner mesh, as shown in FIG. 8A and FIG. 8B, is that cut ends of a mesh can be eliminated at the proximal opening of the mesh.

Figure 9A:
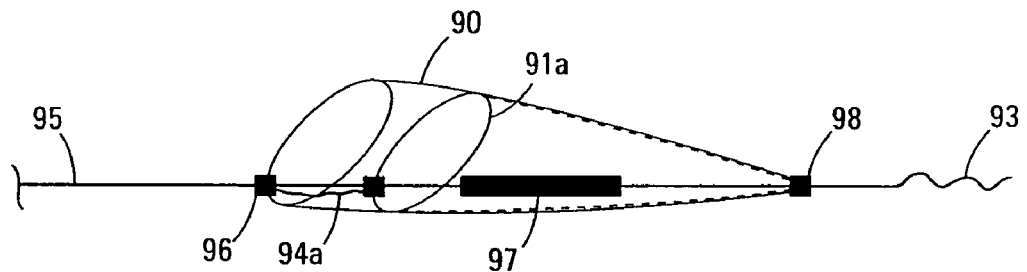
FIGS. 9A to 9C are side views of other embodiments of a filter within filter construction.
Figure 9B:
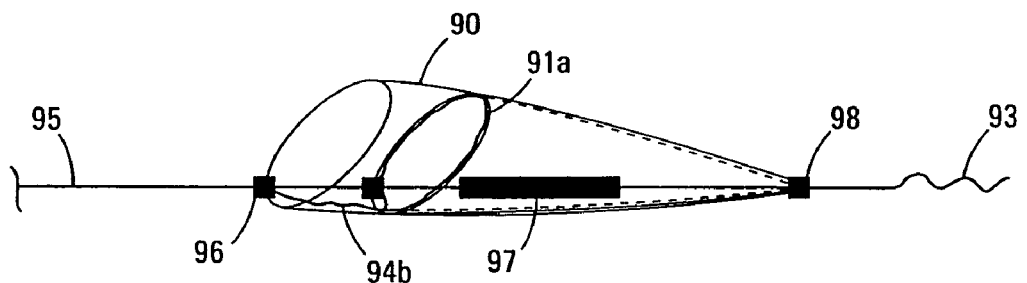
Figure 9C:
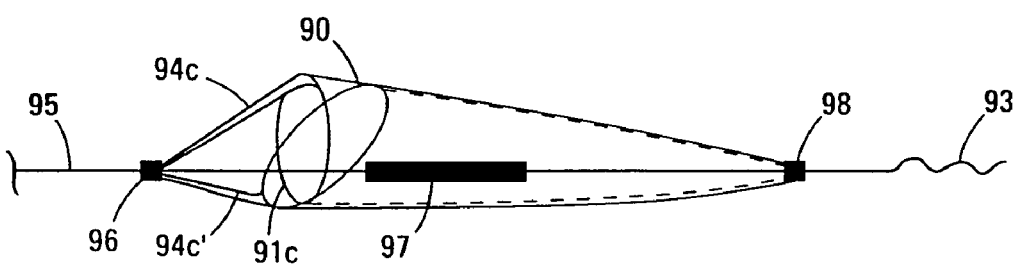

FIGS. 9A to 9C illustrate multiple layer filters in which tethers are used to prohibit distal migration of the inner filter portion when the filter is recovered. FIG. 9A shows outer filter portion 90 and inner filter portion 91a joined at distal sliding element 98 and disposed about elongate support element 95. Proximal sliding element 96 is affixed to filter 90. Stop 97 may be provided, mounted on elongate support element 95, which terminates at floppy tip 93. Inside filter 90, inner filter portion 91a is affixed by tether 94a to proximal slider 96. FIG. 9B shows another embodiment, in which tether 94b comprises a loop, which is affixed to inner filter portion 91b and to proximal slider 96. Inner filter portion 91b is inside of outer filter 90. In this embodiment, inner filter 91b is preferably a rolled back filter and tether 94b functions as a drawstring for closing inner filter 91b. In FIG. 9C, the inner filter portion 91c extends proximally beyond the proximal end of filter portion 90, and is joined by tether 94c to proximal sliding element 96. A second tether, 94c', joins outer filter 90 to proximal sliding element 96. In preferred embodiments, the inner filter portions have smaller average pore sizes than the outer filter portions.

When a filter shown in FIG. 9A, 9B, or 9C is recovered into a catheter, outer filter portion 90 will be drawn into the catheter by elongate member 95 in cooperation with proximal element 96 and possibly stop 97. Typically filter portion 90 will elongate and tension will be applied to tether 94a, b, or c. As the filter is further recovered, tether 94a, b, or c will apply tension to the proximal end of filter portion 91a, b, or c and cause it to be drawn into the recovery catheter. If tethers are not provided there is a tendency for inner filter portions to migrate distally during filter recovery, which can prevent the filter from entering the recovery catheter and can allow captured emboli to be released due to excessive compressive pressure on inner filter portions. Tether properties must be engineered with consideration of the amount of axial stretch during collapse of the inner and outer mesh layers. If both layers stretch the same amount during collapse then the tether can be relatively rigid. If the inner layer stretches less than the outer layer during collapse then the tether must provide a certain amount of elasticity so that the outer layer can fully collapse during recovery. In this situation the tether will provide a limited amount of stretch so that the filter layers can be collapsed yet the inner layer will be prevented from migrating distally.

Figure 10A:
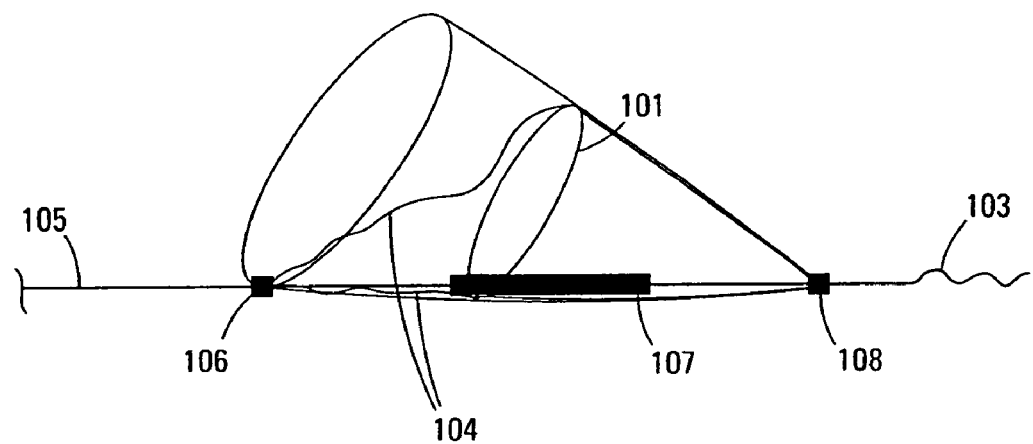
FIG. 10A is a side view of another embodiment of a two layer filter and FIG. 10B is a side view of the filter in its delivery configuration.
Figure 10B:
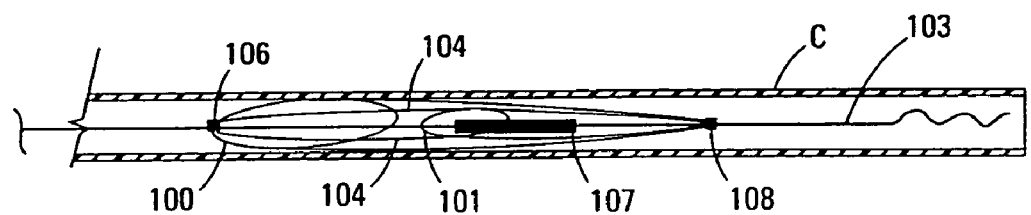

FIGS. 10A and 10B show another variation of a tethered inner filter portion, wherein outer filter portion 100 contains inner filter portion 101, which is tethered to proximal sliding element 106 by tethers 104. Elongate support member 105 terminates at floppy tip 103 and may contain slider 107. FIG. 10B illustrates a delivery configuration of the filter, showing that tethers 104 are fully extended in catheter C. In preferred embodiments, the inner filter portions have smaller average pore sizes than the outer filter portions. This filter is recovered in much the same manner as the filters in FIGS. 9A to 9C.

Figure 11A:
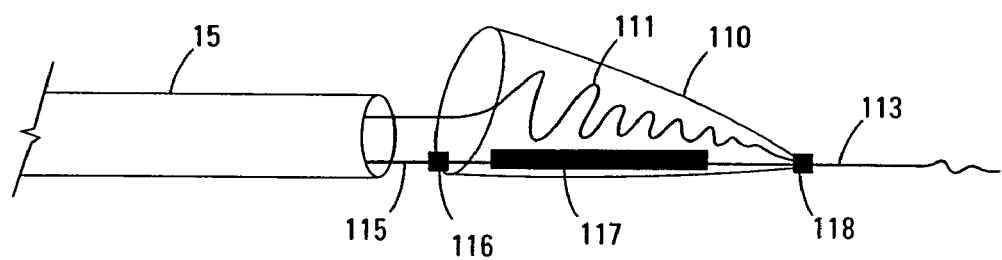
FIGS. 11A and 11B are side views of another embodiment of a two layer filter.
Figure 11B:
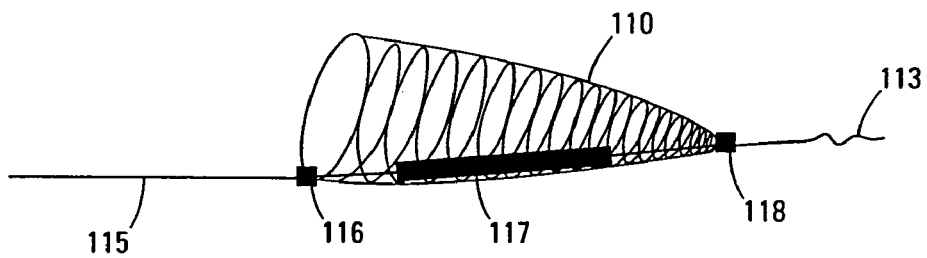

FIGS. 11A and 11B illustrate a tapered spring inside an outer filter. This design is particularly useful for obtaining a small collapsed profile of the filter. The outer filter portion may comprise sparse braid. FIG. 11A illustrates inner spring portion 111 exiting delivery catheter 15 and unwinding within outer filter 110. Preferably inner spring portion 111 is pre-programmed to unwind into a densely packed coil. Catheter 15 may be provided with a pusher to assist with delivery of inner spring portion 111 into outer filter 110. Proximal sliding element 116 is affixed to elongate support member 115 which extends out of the delivery catheter. Spring portion 111 and outer filter 110 are affixed to distal sliding element 118. The support member may contain stop 117 and terminates distally at floppy tip 113. FIG. 11B shows inner spring element 111 completely deployed and the catheter withdrawn. In a preferred embodiment, the inner spring portion 111 can be made out of nitinol wire having a diameter of 0.005 inch (127 micron), with about a 100 micron spacing between the coils. This filter can be recovered in a manner similar to that described in connection with FIGS. 4A to 4C.

Filters Having an Attached Polymeric Film

Figure 12A:
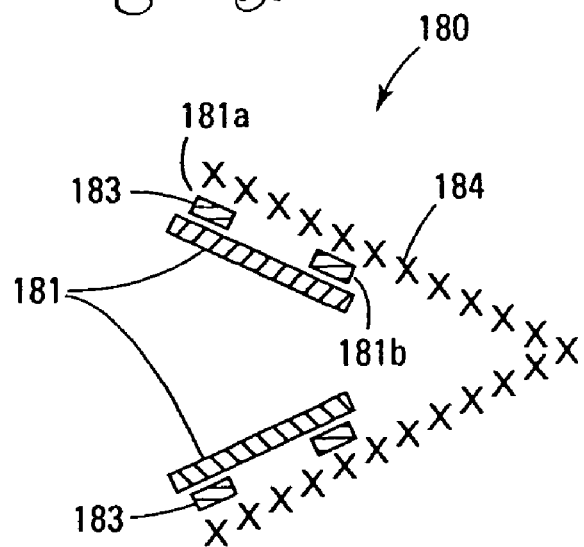
FIGS. 12A and 12B are cross-sectional views of an alternate embodiment of an embolic protection filter having a polymeric film disposed next to the filter braid.
Figure 12B:
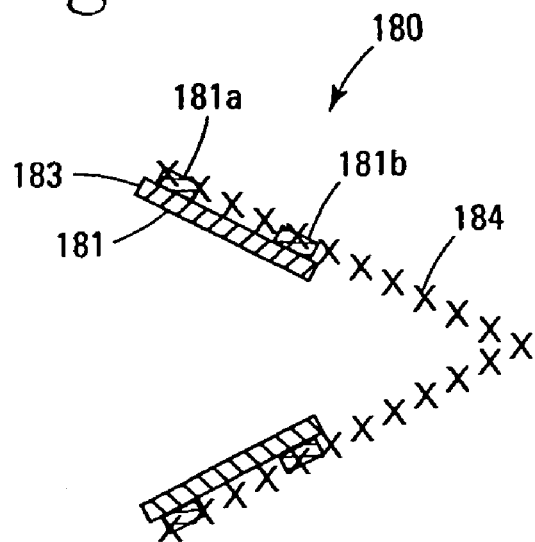

FIGS. 12A and 12B illustrate a polymeric mesh or film attached to an outer filter mesh 184 such as a metallic braid. Filter 180 is shown in cross section. Film 181, such as a polyurethane thermoplastic elastomeric film, is attached at the proximal (181a) and optionally at the distal ends (181b). Optionally, a section of polymer 183 can be interspersed between the filter and the film 181. FIG. 12A shows the film in position next to the filter, and FIG. 12B shows the film as fused to the filter mesh, typically by application of heat. The film need not be so fused elsewhere along its length and need not be fused at any particular location, although it is preferred to fuse the proximal end of the film to the outer filter mesh 184. Preferably the film is extensible so as to not restrict collapse and expansion of filter 180. The film could be positioned inside the outer filter mesh 184 as shown in FIGS. 12A and 12B or positioned outside the outer filter mesh 184. Optionally, a non-extensible film such as ePTFE (expanded polytetrafluoroethylene) can be used and provided with pleats, folds, or sufficient thinness such that the film accommodates outer filter motion without dehiscence during filter deployment, use, and recovery. The film could be impermeable or could be porous.

Attachments and Details for Multi-Layer Traps

Figure 13A:
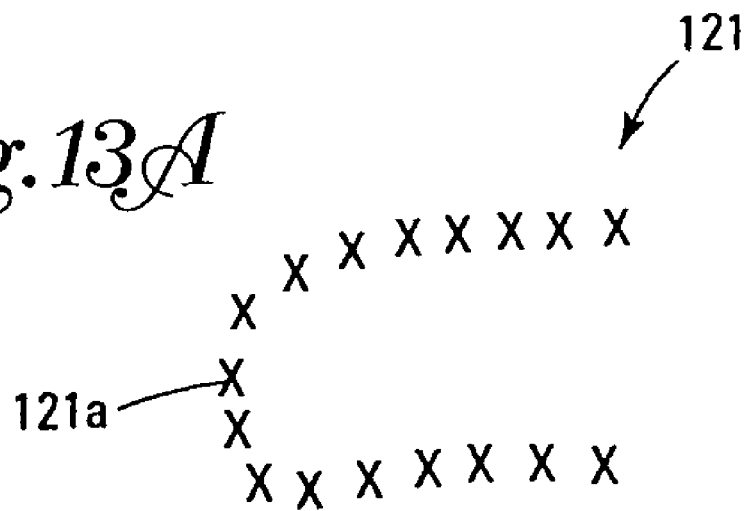
FIG. 13A is a detail cross section schematic view of a portion of a rolled-over mesh.
Figure 13B:
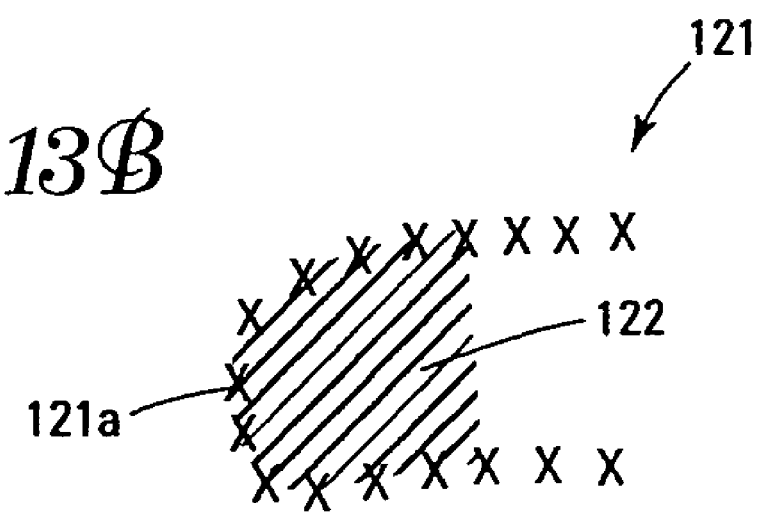
FIG. 13B is a detail cross section schematic view of a polymer layer on this portion.

FIGS. 13A and 13B illustrate filter mesh 121 at the region where the braid is rolled over, 121a. In the rolled back designs, it is desirable to introduce memory of the shape of the rollover region. When nitinol is used, the shape memory can be set by heat. Heat is applied locally to create a zone of preferential bending. The temperature of heat setting can be altered to remove or reduce spring properties at the rollover point. Heat can be applied by laser, by use of a hot plate, a fluidized bed, hot fluid, or other suitable means. However, not all materials can be heat set, and even with heat setting, the desired shape may not be obtained. FIG. 13B shows the roll over region having a polymer layer added. For example, polymer 122 comprising silicone would serve to keep the filter mesh in its proper configuration. Other suitable elastomeric polymers include urethanes, rubbers, and the like, that could be thermoformed onto the rollover region.

Figure 14A:
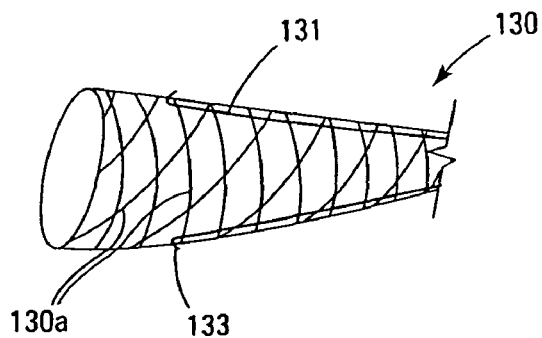
FIG. 14A is a side view of another embodiment of a two layer filter.
Figure 14B:
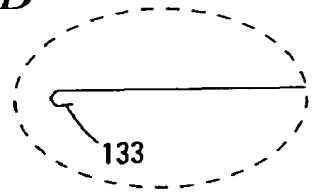
FIGS. 14B to 14F are detail side views of a hook of the inner filter layer.
Figure 14D:
Figure 14C:
Figure 14E:
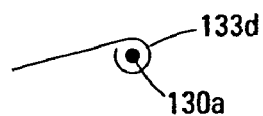
Figure 14F:
Figure 15A:
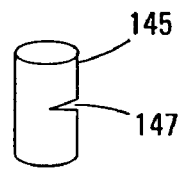
FIG. 15 is a perspective view of a joining component.
FIG. 15B is a perspective view of wires held within the joining component.
Figure 15B:
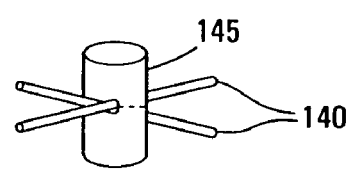

For many of the multilayer filter configurations described above, it is desirable to attach the layers together to prevent emboli from passing between the layers, to register the layers for programming effective filter pore size, to prevent filter layers from separating during recovery, use, or deployment, or to preserve a self-expanding characteristic of the filter by attaching a self expanding layer to a non-self expanding layer. One way to do this is shown in FIG. 14A, where for clarity only the outer filter is shown having mesh, represented by wires. Filter 131 is held within outer filter 130 by hooks 133 that hook onto the mesh of filter 130, shown in FIG. 14A as hooking around one or more of the wires 130a making up filter 130. A detail view of one hook 133, useful for an inner mesh strand in tension, is shown in FIG. 14B. FIG. 14C shows an alternate shape, hook 133c, useful for a mesh strand in compression. FIG. 14D shows hook 133d hooked around wire 130a, in an open configuration, and FIG. 14E shows hook 133d in a closed configuration. These hooks can be relatively insensitive to the axial force on the mesh strand. The hooks also may be provided with a ball (such as ball 134 shown in FIG. 14F) at the end or along the hooking structure in order to reduce the chance of trauma to body tissues and/or to interdigitate with a filter layer so as to attach the layers primarily through entanglement.

FIGS. 15 to 18 describe various ways to join layers in a multilayer filter construction. FIG. 15A shows joining component 145, a cylindrical body having slit 147 in which braid or wire of a filter is placed. The slit is then crimped shut, as illustrated in FIG. 15B, which shows wires 140 affixed in the slit. During or after crimping the joining component may be further deformed or material removed such that edges or roughness may be removed so as to render the structure suitable for use in the human body. Typically the joining component is formed of a malleable material, such as metal, and may be radiopaque. Suitable materials include platinum, gold, platinum-iridium alloy, stainless steel, liquid crystal polymer, PEEK, and the like. The slit may be a slot having greater width to accommodate the mesh structures to be joined. Although wires are illustrated in FIGS. 15A and 15B, it is contemplated that these joining structures can be utilized with a wide range of mesh structures including films and laser cut tubular structures.

Figure 16A:
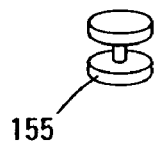
FIG. 16A is a perspective view of a rivet.
Figure 16B:
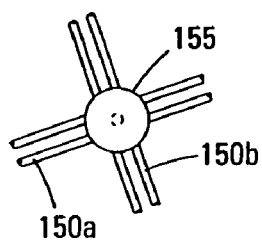
FIG. 16B is a top view of wires in two layers attached by the rivet.
Figure 16C:
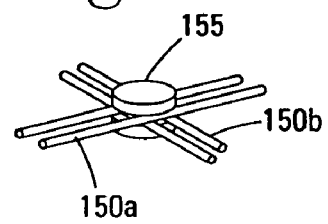
FIG. 16C is a perspective view of wires held by the rivet.

FIG. 16A shows rivet 155 that is used to join braid or wire layers 150a and 150b, shown in top view in FIG. 16B. FIG. 16C shows a perspective view of multiple wires attached by the rivet. Rivets are sized to fit the mesh of the filter and typically are constructed of materials similar to those described in connection with FIGS. 15A and 15B. It is envisioned that these rivets will be used and processed as described in connection with FIGS. 15A and 15B.

Figure 17A:
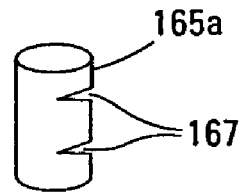
FIGS. 17A and 17B are perspective view of another embodiment of a joining component.
Figure 17B:
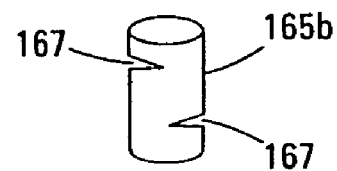

FIGS. 17A and 17B show other variations in a cylindrical joining component. Component 165a has two slits 167 on the same side of the cylinder, and in FIG. 17B, component 165b has two slits 167 offset and opposed to each other.

Figure 18A:
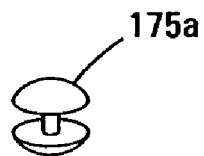
FIGS. 18A to 18C are perspective views of other embodiments of rivets.
Figure 18B:
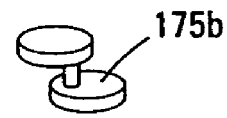
Figure 18C:
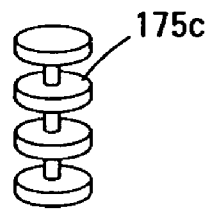

FIGS. 18A to 18C show various rivets 175a, 175b, and 175c, respectively, that can join layers together. Rivet 175 has curved top and bottom surfaces and is symmetrical about central axis. Rivet 175b is asymmetrical. Rivet 175c is suitable for joining at least three layers together.

In addition to the methods described above, the pore sizes of the filters and filtering layers described above can also be controlled by the methods described in the U.S. patent application filed on the same date as the present application and entitled "Embolic Filters With Controlled Pore Size" Ser. No. 10/354,679, the contents of which are hereby incorporated by reference herein.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A device for filtering emboli from blood flowing through a lumen defined by the walls of a vessel in a patient's body, comprising:
    a filter element being expandable from a collapsed configuration to an expanded configuration, wherein when the filter element is in the expanded configuration, the average pore size is from 30 to 300 microns and the standard deviation of the pore size is less than 20 percent of the average pore size, and wherein the filter element comprises two or more filtering layers, each filtering layer comprising pores, and at least one filtering layer being in substantial contact with at least one other filtering layer.

2. A device of claim 1, wherein when the filter element is in the expanded configuration, the average pore size is from 30 to 150 microns.

3. A device of claim 1, wherein when the filter element is in the expanded configuration, the average pore size is from 100 to 140 microns.

4. A device of claim 1, wherein when the filter element is in the expanded configuration, the average pore size is from 40 to 70 microns.

5. A device of claim 1, wherein when the filter element is in the expanded configuration, the standard deviation of the pore size is less than 15 percent of the average pore size.

6. A device of claim 1, wherein when the filter element is in the expanded configuration, the standard deviation of the pore size is less than 10 percent of the average pore size.

7. A device of claim 1, wherein when the filter element is in the expanded configuration, the standard deviation of the pore size is less than 5 percent of the average pore size.

8. A device of claim 1, wherein when the filter element is in the expanded configuration, the standard deviation of the pore size is less than 2 percent of the average pore size.

9. A device of claim 1, wherein when the filter element is in the expanded configuration, the filter element has a percent open area greater than 50 percent.

10. A device of claim 1, wherein when the filter element is in the expanded configuration, the filter element has a percent open area greater than 60 percent.

11. A device of claim 1, wherein when the filter element is in the expanded configuration, the filter element has a percent open area greater than 70 percent.

12. A device of claim 1, wherein when the filter element is in the expanded configuration, the filter element has a percent open area greater than 80 percent.

13. A device of claim 1, wherein at least one of the filtering layers has a tensile strength greater than 70,000 psi.

14. A device of claim 1, wherein at least one of the filtering layers has a tensile strength greater than 100,000 psi.

15. A device of claim 1, wherein at least one of the filtering layers has a tensile strength greater than 200,000 psi.

16. A device of claim 1, wherein at least one of the filtering layers is made of metal.

17. A device of claim 1, wherein at least one of the filtering layers is made of nitinol.

18. A device of claim 1, further comprising an elongate support member and wherein the filter element is carried on a portion of the elongate support member.

19. A device of claim 1, wherein the filter element has proximal and distal portions and a central portion, the filter element having a shape in the expanded configuration which defines a cavity having a proximal facing opening.

20. A device of claim 19, wherein at least one of the filtering layers comprises wires braided to form diamond-shaped pores.

21. A device of claim 1, wherein the filter element comprises a mesh rolled back on itself to form two filtering layers.

22. A device of claim 21, wherein the filter element has proximal and distal portions and a central portion, the filter element having a shape in the expanded configuration which defines a cavity having a proximal facing opening.

23. A device of claim 22, wherein the filter element comprises a drawstring tether at the proximal facing opening of the filter element.

24. A device of claim 22, wherein at least one of the filtering layers comprises wires braided to form diamond-shaped pores.

25. A device of claim 1, wherein the filter element comprises two separate filtering layers.

26. A device of claim 25, wherein the filter element has proximal and distal portions and a central portion, the filter element having a shape in the expanded configuration which defines a cavity having a proximal facing opening.

27. A device of claim 25, wherein at least one of the filtering layers comprises wires braided to form diamond-shaped pores.

28. A device of claim 25, wherein the two separate filtering layers have different average pore sizes.

29. A device of claim 25, wherein the two separate filtering layers are not attached to each other.

30. A device of claim 25, wherein the two separate filtering layers are attached to each other.

31. A device of claim 30, wherein the two separate filtering layers are attached to each other by a fixed element.

32. A device of claim 30, wherein the two separate filtering layers are attached to each other by a sliding element.

33. A device of claim 30, wherein the two separate filtering layers are attached to each other by a tether.

34. A device of claim 25, wherein a first filtering layer comprises wires braided to from diamond-shaped pores, and the second filtering layer comprises a coiled wire.

* * * * *